(12) United States Patent
Singh et al.

(10) Patent No.: US 9,421,293 B2
(45) Date of Patent: Aug. 23, 2016

(54) FILTRATION MEDIUM WITH ELECTROSPUN METAL OXIDE NANOFIBER LAYER

(75) Inventors: Gurdev Singh, Singapore (SG); Anbharasi Vanangamudi, Singapore (SG); James Antony Prince, Singapore (SG)

(73) Assignee: Ngee Ann Polytechnic, Singapore (SG)

( * ) Notice: Subject to any disclaimer, the term of this patent is extended or adjusted under 35 U.S.C. 154(b) by 0 days.

(21) Appl. No.: 14/394,449

(22) PCT Filed: Apr. 17, 2012

(86) PCT No.: PCT/SG2012/000134
§ 371 (c)(1),
(2), (4) Date: Dec. 29, 2014

(87) PCT Pub. No.: WO2013/158028
PCT Pub. Date: Oct. 24, 2013

(65) Prior Publication Data
US 2015/0250910 A1    Sep. 10, 2015

(51) Int. Cl.
*A62B 7/08* (2006.01)
*B01D 50/00* (2006.01)
(Continued)

(52) U.S. Cl.
CPC ............... *A61L 2/238* (2013.01); *A61L 2/022* (2013.01); *A61L 2/232* (2013.01); *A62D 9/00* (2013.01); *B01D 39/163* (2013.01); *B01D 53/38* (2013.01);
(Continued)

(58) Field of Classification Search
CPC ............ A61L 9/00; A61L 9/03; A61L 9/205; F24F 13/28; F24F 3/16; B01J 20/00; B01J 35/004

USPC ............. 423/10; 422/120, 312; 55/318, 489; 95/133, 287; 96/121, 134, 224; 424/76.2; 252/62.3 R

See application file for complete search history.

(56) References Cited

U.S. PATENT DOCUMENTS

| 7,211,707 B2 | 5/2007 | Axtell et al. |
| 2006/0068668 A1 | 3/2006 | Kameoka et al. |

(Continued)

FOREIGN PATENT DOCUMENTS

| IT | WO 2008/145175 A1 * | 12/2008 | ............. A62B 23/02 |
| WO | 03000328 A1 | 1/2003 | |

(Continued)

OTHER PUBLICATIONS

International Preliminary Report on Patentability for International Application PCT/SG2012/000134, Report Issued Oct. 21, 2014, 5 pgs.

(Continued)

*Primary Examiner* — Monzer R Chorbaji
(74) *Attorney, Agent, or Firm* — KPPB LLP

(57) ABSTRACT

A multi-layered filtration medium for detoxification of chemical contaminants and disinfection of biological contaminants. The filtration medium includes two disinfection nanofiber layers and one detoxification nanofiber layer disposed between the two disinfection nanofiber layers. The filtration medium is loaded with high content of a detoxifying material which capable of achieving about 95% detoxification efficiency with no leaching of the detoxifying material. The filtration medium may also include a medicinal substance for medical applications and a sensor for indicating the lifetime of the filtration medium.

40 Claims, 14 Drawing Sheets

(51) Int. Cl.
  *B01D 53/02* (2006.01)
  *A61L 2/238* (2006.01)
  *A62D 9/00* (2006.01)
  *B01D 53/38* (2006.01)
  *B32B 5/26* (2006.01)
  *D01D 5/00* (2006.01)
  *B01D 53/82* (2006.01)
  *B01D 39/16* (2006.01)
  *A61L 2/02* (2006.01)
  *A61L 2/232* (2006.01)
  *D01F 1/10* (2006.01)
  *D01F 8/04* (2006.01)

(52) U.S. Cl.
  CPC ............... *B01D 53/82* (2013.01); *B32B 5/26* (2013.01); *D01D 5/0007* (2013.01); *B01D 2239/025* (2013.01); *B01D 2239/0258* (2013.01); *B01D 2239/0442* (2013.01); *B01D 2239/065* (2013.01); *B01D 2239/086* (2013.01); *B01D 2251/602* (2013.01); *B01D 2253/104* (2013.01); *B01D 2255/104* (2013.01); *B01D 2257/70* (2013.01); *B01D 2257/91* (2013.01); *B01D 2257/93* (2013.01); *B01D 2258/06* (2013.01); *B01D 2259/4541* (2013.01); *D01F 1/10* (2013.01); *D01F 8/04* (2013.01)

(56) References Cited

U.S. PATENT DOCUMENTS

| | | |
|---|---|---|
| 2007/0181001 A1 | 8/2007 | Bohringer et al. |
| 2008/0264259 A1 | 10/2008 | Leung |
| 2010/0009267 A1 | 1/2010 | Chase et al. |
| 2010/0050872 A1 | 3/2010 | Lee |
| 2010/0113857 A1 | 5/2010 | Ramakrishna et al. |
| 2010/0233812 A1 | 9/2010 | Sun et al. |
| 2010/0307119 A1 | 12/2010 | Leung et al. |

FOREIGN PATENT DOCUMENTS

| | | |
|---|---|---|
| WO | 2004114256 A2 | 12/2004 |
| WO | 2007054040 A2 | 5/2007 |
| WO | 2008145175 A1 | 12/2008 |

OTHER PUBLICATIONS

International Search Report and Written Opinion for International Application No. PCT/SG2012/000134, Search completed Jul. 9, 2012, Mailed Jul. 10, 2012, 7 Pgs.

* cited by examiner

FILTRATION MEDIUM WITH ELECTROSPUN METAL OXIDE NANOFIBER LAYER

FIELD OF THE INVENTION

The present invention relates to filtration medium and method of making the same. More particularly, the present invention relates to a filtration medium that decontaminates both chemical and biological agents. Still more particularly, the present invention relates to a multi-layered filtration medium that includes two nanofiber layers with each layer comprising a metal compound for disinfection of biological agents, and a middle nanofiber layer comprising a metal oxide compound for detoxification of chemical agents.

BACKGROUND OF THE INVENTION

Chemical and biological agents (or contaminants) pose many adverse effects and health threats to humans and animals. These contaminants may be in a fluid form (e.g. gas, liquid, or gel) or a solid form (e.g. powder). Chemical contaminants include nerve agents, blister/percutaneous agents, and blood agents. Nerve agents attack human body and interfere with nervous system via immobilization of key enzymes. Blister/percutaneous agents attack the skin and/or mucous membranes tissues external and/or internal to human body. Biological contaminants include bacteria, viruses, fungi and spores, which may also attack human body. Thus, these harmful chemical and biological contaminants have to be filtered and/or eliminated so as to prevent them from attacking human body.

Face masks with limited filtering capacity, such as N95 and surgical masks, are commonly used to protect human from pathogens. These face masks and normal filters neither detoxify chemical contaminants nor disinfect biological contaminants. Hence, various filtration techniques and products have been explored and introduced to eliminate chemical and/or biological contaminants. Such a protective material is described for example in US 2010/0113857 A1, which discloses a nano-sized fiber comprising metal oxide nanoparticles for detoxifying a toxic agent. The weight ratio of metal oxide nanoparticles to polymer of the nanofiber is about 1:10. Another example is described in US 2008/0264259 A1, which discloses a filtration medium that includes a fine filter layer and a coarse filter layer. The fine filter layer comprises anti-microbial nanoparticles of about 0.1 weight percent (wt %) to 10 wt %.

For the above examples and other prior art, the content of the detoxifying material in a filtration medium is relatively low (e.g. below 15 wt %) and may be toxic. Hence, it is important to prevent leaching of this material from the medium. It is important to note that simply increasing the loading of the detoxifying material in a filtration medium without careful considerations of the structure of the filtration medium and the processes of making the filtration medium would lead to leaching of the detoxifying material which is undesirable. Further, it is not easy to synthesize a uniform or homogenous nanofiber layer from a solution with high loading of a detoxifying material. Hence, a need exists for a filtration medium with highly improved detoxification efficiency and at the same time does not impose any risks and adverse effects to the users of the filtration medium.

SUMMARY OF THE INVENTION

The above and other problems are solved and an advance in the art is made by a multi-layered filtration medium that decontaminates both chemical and biological contaminants. Embodiments of a filtration medium in accordance with the present invention have many applications, for example, but not limited to, self-decontamination face masks. One advantage of these masks is that the masks are capable of filtering particles and eliminating chemical and biological contaminants so as to prevent wearers from spreading and/or receiving harmful contaminants. Advantages of embodiments of a filtration medium in accordance with this invention include that the medium may be manufactured easily; and may be applied to or incorporated into any commercial filters so as to provide detoxification and disinfection functionalities to the commercial filters, as well as to improve their filtration efficiency.

A first particular advantage of a filtration medium in accordance with embodiments of the present invention is the provision of a filtration medium with high loading of a metal oxide compound, i.e. anti-chemical material (e.g. aluminium oxide, $Al_2O_3$), of up to about 67 wt % which capable of detoxifying about 95% of chemical contaminants. This metal oxide compound acts as a catalyst that reacts with chemical contaminants to form intermediates (i.e. chemical by-products) in transition states. In other words, chemical contaminants are detoxified or decomposed by the metal oxide compound into chemical entities that are non-toxic or less toxic. In addition, the filtration medium also has excellent disinfection properties that are capable of destroying or eliminating biological contaminants by having a metal compound (e.g. silver) that has a toxic effect on microbial organisms.

A second advantage of a filtration medium in accordance with embodiments of the present invention is that the filtration medium has a fast detoxification reactivity in a relatively short period of time due to high loading of detoxifying nanoparticles, large surface area-to-volume ratio of detoxifying nanoparticles, and nanometer-sized fibers of the filtration medium. Particularly, the filtration medium is capable of achieving about 95% detoxification of chemical contaminants and about 100% disinfection of biological contaminants, in a relative short period of time (e.g. less than 60 minutes).

A third advantage of a filtration medium in accordance with embodiments of the present invention is that there is no leaching of detoxifying (i.e. anti-chemical) material and disinfecting (i.e. anti-biological) material from the medium. Thus, the medium provides a safe usage environment for the users. This non-leaching property is due to strong bonding of the detoxifying and disinfecting materials with the nanofibers of the filtration medium. Apart from strong bonding, the filtration medium is configured with the detoxification layer sandwiched between two disinfection layers. This configuration helps to prevent leaching of the detoxifying material.

A fourth advantage of a filtration medium in accordance with embodiments of the present invention is the provision of a filtration medium which is durable and capable of detoxifying chemical contaminants in multiple times. This is because the detoxifying material acts as a catalyst that can be regenerated during detoxification process. In addition, the filtration medium may include a membrane sensor for indicating the lifetime of the filtration medium in accordance with some embodiments of mediums in accordance with this invention.

A fifth advantage of a filtration medium in accordance with embodiments of the present invention is the provision of a filtration medium incorporated with a medicinal substance for medical applications. To prevent leaching of the medicinal substance, the medicinal substance is coated by a polymer that can be prepared with a core-shell electrospinning method in accordance with some embodiments of this invention.

A sixth advantage of a filtration medium in accordance with embodiments of the present invention is the provision of a filtration medium with good permeability to airflow, i.e. good breathability with pressure drop of less than 300 Pa. In addition, the filtration medium is lightweight, flexible and can be configured into a desired shape and applied to any commercial filter so as to improve filtration efficiency of the filter with additional detoxification and disinfection properties.

In the context of this specification, the term "nanofiber" is used to represent a filament having an average diameter less than about 1,000 nanometers (nm), preferably from about 1 nm to about 100 nm. The term "about", in the context of concentration of a compound or efficiency of a process/reactivity, typically means ±2% of the stated value, more typically means ±1% of the stated value, even more typically ±0.5% of the stated value.

According to a first aspect of embodiments of the present invention, there is provided a filtration medium with protective function against chemical and biological contaminants. The filtration medium in accordance with these embodiments comprises a first nanofiber layer, a second nanofiber layer, and a middle nanofiber layer disposed between the first and second nanofiber layers. The first nanofiber layer comprises a first metal compound and a first binder for covalently bonding with the first metal compound. The first metal compound is in an ionic form is capable of attracting and destroying the biological contaminants. The second nanofiber layer comprises a second metal compound and a second binder for covalently bonding with the second metal compound. The second metal compound is in an ionic form is capable of attracting and destroying the biological contaminants. The middle nanofiber layer comprises a metal oxide compound and a polymer which acts as a binder for bonding with the metal oxide compound. The metal oxide compound is capable of reacting with the chemical contaminants through a catalysis mechanism to form at least one chemical by-product and regenerate the metal oxide compound.

In accordance with some embodiments, the content of the metal oxide compound of the middle nanofiber layer is between the range of about 1 wt % to about 67 wt %. The filtration medium with about 67 wt % of the metal oxide compound is capable of achieving about 95% detoxification of the chemical contaminants. In some embodiments, the ratio of the metal oxide compound to the polymer of the middle nanofiber layer is about 67:33 wt %.

In accordance with some embodiments, the content of the first metal compound of the first nanofiber layer is between the range of about 1 wt % to about 12 wt % which is capable of achieving about 100% disinfection of the biological contaminants.

In accordance with some embodiments, the content of the second metal compound in the second nanofiber layer is between the range of about 1 wt % to about 12 wt % which is capable of achieving about 100% disinfection of the biological contaminants.

In accordance with some embodiments, the first nanofiber layer comprises a plurality of first nanofibers with each first nanofiber having a plurality of first metal nanoparticles made of the first metal compound.

In accordance with some embodiments, the second nanofiber layer comprises a plurality of second nanofibers with each second nanofiber having a plurality of second metal nanoparticles made of the second metal compound.

In accordance with some embodiments, the middle nanofiber layer comprises a plurality of middle nanofibers with each middle nanofiber having a plurality of metal oxide nanoparticles made of the metal oxide compound. The size of each of the plurality of metal oxide nanoparticles determines the rate of the catalysis mechanism. The number of the plurality of metal oxide nanoparticles determines the rate of the catalysis mechanism.

In accordance with some embodiments, the thickness of the first nanofiber layer is between the range of 5 μm to 100 μm, the thickness of the second nanofiber layer is between the range of 5 μm to 100 μm, and the thickness of the middle nanofiber layer is between the range of 10 μm to 100 μm.

In accordance with some embodiments, the first metal compound comprises silver, the second metal compound comprises silver, and the metal oxide compound comprises aluminium oxide.

In accordance with some embodiments, the chemical contaminants are paraoxon which can be decomposed by aluminium oxide of the middle nanofiber layer to form the at least one chemical by-product that is at least one of p-nitrophenol, ethanol, and orthophosphoric acid.

In accordance with some embodiments, first binder of the first nanofiber layer is a poly(acrylic acid), the second binder of the second nanofiber layer is a poly(acrylic acid), and the polymer of the middle nanofiber layer is a polyvinylidene fluoride.

In accordance with some embodiments, the first nanofiber layer further comprises a first medicinal substance for medical treatment. The outer surface of the first medicinal substance is being coated by at least one polymer.

In accordance with some embodiments, the second nanofiber layer further comprises a second medicinal substance for medical treatment. The outer surface of the second medicinal substance is being coated by at least one polymer.

In accordance with some embodiments, the filtration medium further comprises a membrane sensor that changes colour in response to exposure to carbon dioxide for indicating the lifetime of the filtration medium. The membrane sensor is made of a combination of a plurality of dyes.

In accordance with some embodiments, the first nanofiber layer, the second nanofiber layer, and the middle nanofiber layer are bound together by heat pressing at a temperature between 100° C. and 170° C.

In accordance with some embodiments, the filtration medium is in a form of membrane.

According to a second aspect of the embodiments of the present invention, one method for producing a filtration medium with protective function against chemical and biological contaminants is performed in the following manner. The method begins by forming a first nanofiber layer which comprises a first metal compound and a first binder for covalently bonding with the first metal compound. The method then forms a middle nanofiber layer which comprises a metal oxide compound and a polymer which acts as a binder for bonding with the metal oxide compound. A second nanofiber layer is then formed which comprises a second metal compound and a second binder for covalently bonding with the second metal compound. The first nanofiber layer is bound to a first side of the middle nanofiber layer, and the second nanofiber layer is bound to a second side of the middle nanofiber layer.

In accordance with some embodiments, the step of forming the first nanofiber layer comprises performing an electrospinning a mixture comprises the first metal compound, the first binder and a polymer to form a plurality of first nanofibers.

In accordance with some embodiments, the step of forming the second nanofiber layer comprises performing an electrospinning a mixture comprises the second metal compound, the second binder and a polymer to form a plurality of second nanofibers.

In accordance with some embodiments, the step of forming the middle nanofiber layer comprises performing an electrospinning a mixture comprises the metal oxide compound and the polymer to form a plurality of middle nanofibers.

In accordance with some embodiments, the step of binding the first nanofiber layer to the first side of the middle nanofiber layer comprises performing a heat pressing the first nanofiber layer to the middle nanofiber layer at a temperature between 100° C. and 170° C.

In accordance with some embodiments, the step of binding the second nanofiber layer to the second side of the middle nanofiber layer comprises performing a heat pressing the second nanofiber layer to the middle nanofiber layer at a temperature between 100° C. and 170° C.

In accordance with some embodiments, the method of producing the filtration medium may include a step of adding a first medicinal substance to the first nanofiber layer. The step comprises performing a core-shell electrospinning the first medicinal substance and a polymer to form a plurality of medicated nanofibers. The first medicinal substance forms the core of each of the plurality of medicated nanofibers and the polymer forms the shell of each of the plurality medicated nanofibers.

In accordance with some embodiments, the step of adding the first medicinal substance to the first nanofiber layer comprises performing a core-shell electrospinning the first medicinal substance and a first mixture comprises the first metal compound, the first binder and a polymer to form a plurality of medicated nanofibers. The first medicinal substance forms the core of each of the plurality of medicated nanofibers and the first mixture forms the shell of each of the plurality of medicated nanofibers.

In accordance with some embodiments, the method of producing the filtration medium may include a step of adding a second medicinal substance to the second nanofiber layer. The step comprises performing a core-shell electrospinning the second medicinal substance and a polymer to form a plurality of medicated nanofibers. The second medicinal substance forms the core of each of the plurality of medicated nanofibers and the polymer forms the shell of each of the plurality of medicated nanofibers.

In accordance with some embodiments, the step of adding the second medicinal substance to the second nanofiber layer comprises performing a core-shell electrospinning the second medicinal substance and a second mixture comprises the second metal compound, the second binder and a polymer to form a plurality of medicated nanofibers. The second medicinal substance forms the core of each of the plurality of medicated nanofibers and the second mixture forms the shell of each of the plurality of medicated nanofibers.

In accordance with some embodiments, an article may comprise a filtration medium as described above or comprise a filtration medium made by the processes as described above. The article may be used for detoxifying chemical and biological contaminants.

BRIEF DESCRIPTION OF THE DRAWINGS

The present invention will now be described, by way of examples only, with reference to the accompanying drawings, in which.

DETAILED DESCRIPTION OF THE INVENTION

Embodiments of the present invention relate to a multi-layered filtration medium that includes at least two disinfection (anti-biological) nanofiber layers and at least one detoxification (anti-chemical) nanofiber layer disposed between the two disinfection nanofiber layers. Although a filtration medium with three nanofiber layers is discussed in this specification, the number of detoxification and disinfection nanofiber layers may be varied in some embodiments without departing from this invention.

Figure 1:
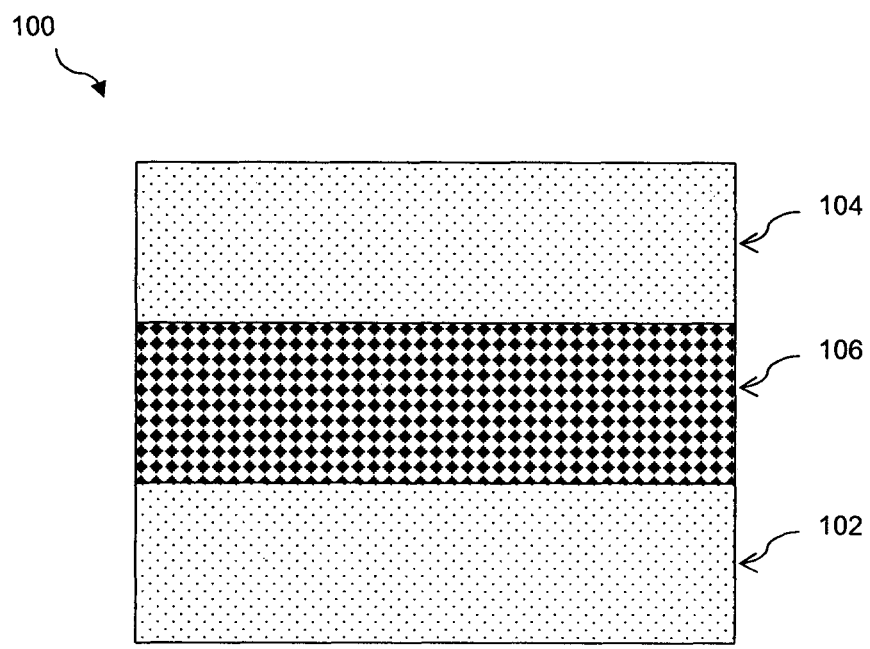
FIG. 1 is a sectional view of a filtration medium according to an embodiment of the present invention.
Figure 14:
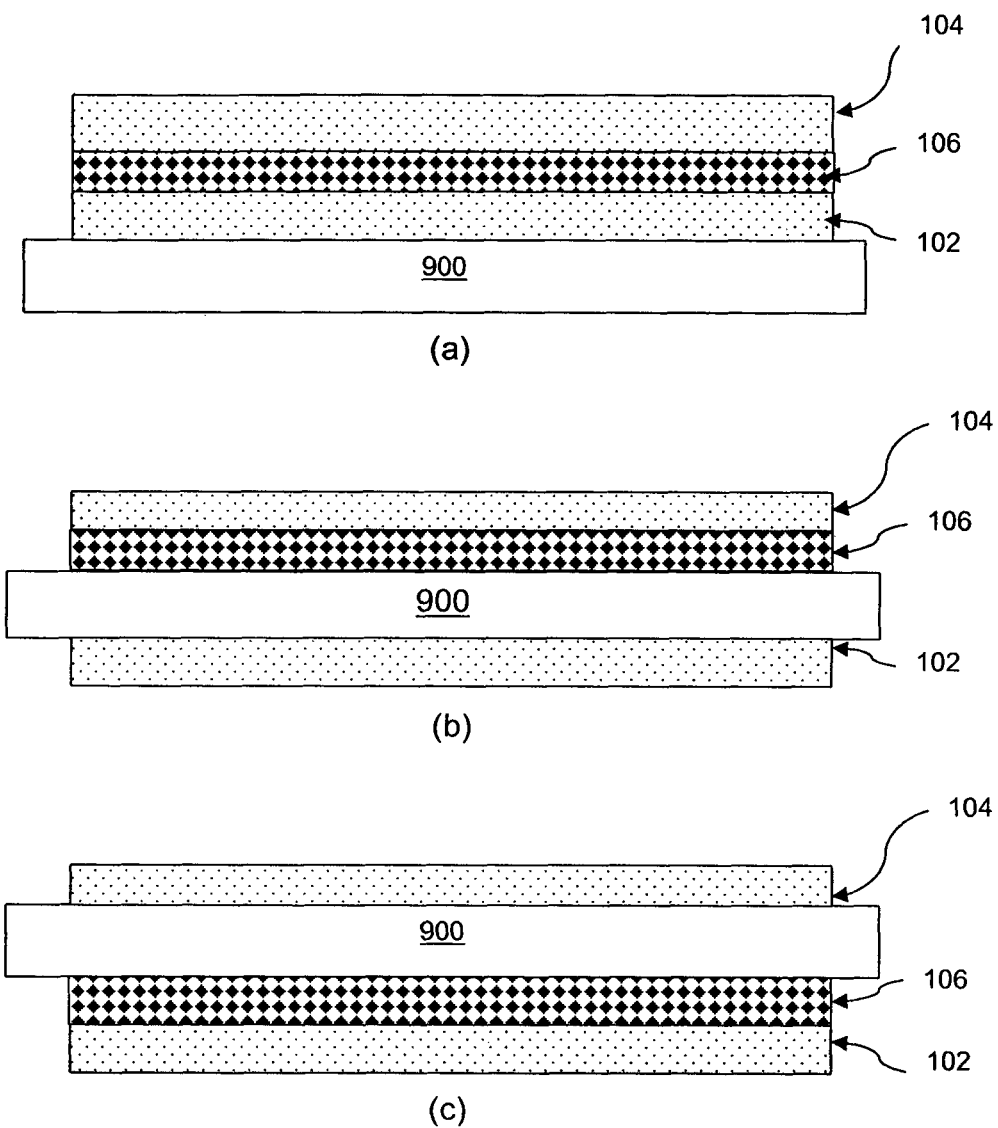
FIG. 14 illustrates various sectional views of an article incorporated with a filtration medium according to an embodiment of the present invention.

FIG. 1 shows a sectional view of filtration medium 100 with protective function against both chemical and biological contaminants in accordance with an embodiment of the present invention. Filtration medium 100 comprises first nanofiber layer 102, second nanofiber layer 104, and middle nanofiber layer 106 disposed between first nanofiber layer 102 and second nanofiber layer 104. These three nanofiber layers 102, 104 and 106 are bound together by a suitable binding process, for example heat pressing at a temperature between 100° C. and 170° C. for about 15 to 20 minutes, to form a bi-functional filtration medium that capable of detoxifying chemical contaminants as well as disinfecting biological contaminations. Filtration medium 100 is preferably in a form of membrane and can be applied to or incorporated into an article, e.g. any commercial filters such as N95 mask and surgical mask. For example, filtration medium 100 can be incorporated into commercial filter 900 to form various configurations as shown in FIG. 14. (a) to (c). Once skilled in the art will recognize that other configurations are also possible.

Middle nanofiber layer 106 comprises a metal oxide compound and a polymer which acts as a binder for bonding the metal oxide compound to middle nanofiber layer 106. The thickness of middle nanofiber layer 106 is preferably in the range of about 10 µm to about 100 µm (a thickness of above 100 um is also possible). The polymer which acts as a binder can be any suitable material, e.g. polyvinylidene fluoride ("PVDF"). The arrangement of middle nanofiber layer 106 sandwiched between first nanofiber layer 102 and second nanofiber layer 104 protects middle nanofiber layer 106 and prevents leaching of the metal oxide compound. The metal oxide compound can be any suitable detoxifying (anti-chemical) material, e.g. $Al_2O_3$, MgO, ZnO, $TiO_2$ and $Fe_2O_3$, that is capable of reacting with chemical contaminants through a catalysis mechanism to form at least one chemical by-product which is non-toxic or less toxic. In other words, the metal oxide compound acts as a catalyst to decompose chemical contaminants into intermediates in transition states and reproduce the metal oxide compound eventually. The reproduced metal oxide compound can react with the remaining chemical contaminants, and detoxification process repeats. The content of metal oxide compound in middle nanofiber layer 106 determines the rate of catalysis mechanism, i.e. detoxification efficiency of filtration medium 100. Therefore, to improve the detoxification efficiency, the content of metal oxide compound may be increased. In some embodiments, the content of the metal oxide compound of middle nanofiber layer 106 is from about 1 wt % to about 67 wt %. In some embodiments, the ratio of the metal oxide compound to the polymer of middle nanofiber layer 106 is about 67:33 wt %. Filtration medium 100 with 67 wt % of metal oxide compound is capable of detoxifying about 95% of chemical contaminants within a relative short period of time, e.g. less than 60 minutes. Thus, filtration medium 100 is highly efficient in detoxifying chemical contaminants.

Figure 2:
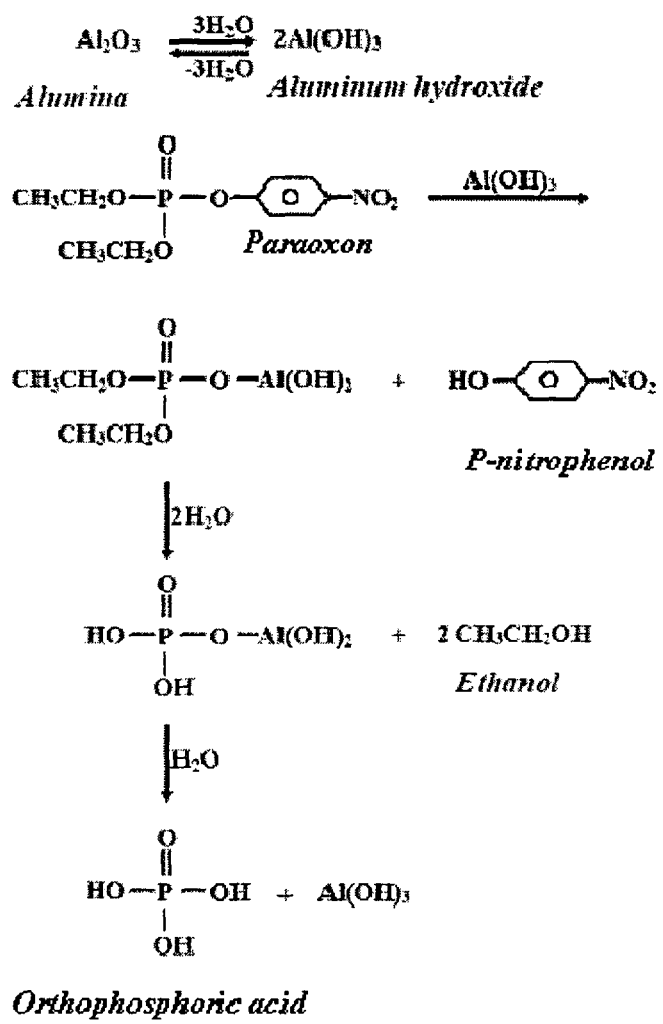
FIG. 2 is a schematic diagram illustrating decomposition of paraoxon (a nerve agent simulant) by aluminium oxide ($Al_2O_3$) in a filtration medium according to an embodiment of the present invention.

The detoxification property of middle, nanofiber layer 106 is described in the following example. As illustrated in FIG. 2, a nerve agent simulant paraoxon (i.e. diethyl 4-nitrophenyl phosphate) is decomposed by $Al_2O_3$ through a hydrolysis reaction to form chemical by-products, namely p-nitrophenol ($C_6H_5NO_3$), ethanol ($C_2H_6O$) and orthophosphoric acid ($H_3PO_4$), in several reaction states. The detoxification process begins with the exposure of $Al_2O_3$ to air ($H_2O$) to produce aluminium hydroxides ($Al(OH)_3$). Aluminium hydroxides react with paraoxon to release p-nitrophenol. Two molecules of ethanol are then released due to the subsequent hydrolysis reaction. Finally, orthophosphoric acid is released and aluminium hydroxide is produced. Although aluminium hydroxide was consumed in the first reaction, it is subsequently produced in the third reaction. By releasing water molecules from aluminium hydroxide, aluminium oxide $Al_2O_3$ is regenerated for next detoxification process.

First nanofiber layer 102 comprises a first metal compound and a first binder for bonding the first metal compound to first nanofiber layer 102. The thickness of first nanofiber layer 102 is preferably in the range of about 5 µm to about 100 µm (a thickness of above 100 um is also possible). The first binder can be any suitable material, e.g. poly(acrylic acid) ("PAA") polymer. The first metal compound can be any suitable disinfecting (anti-biological) material, e.g. silver (Ag), which is capable of disinfecting biological contaminants. The first metal compound in an ionic form (e.g. $Ag^+$) is capable of attracting and destroying biological contaminants. The first metal compound is attached to the first binder by a strong covalent or ionic bonding, without affecting the disinfection properties of the first metal compound. This strong bonding prevents leaching of the first metal compound from first nanofiber layer 102, thereby improves the disinfection efficiency of filtration medium 100 and provides a safe environment for the users. If a toxic first metal compound is used (e.g. silver), leaching of such toxic material is prevented. In some embodiments, the content of first metal compound is from about 1 wt % to about 12 wt % which is capable of achieving about 100% disinfection of biological contaminants. Thus, filtration medium 100 is highly efficient in disinfecting biological contaminants.

Second nanofiber layer 104 comprises a second metal compound and a second binder for bonding the second metal compound to second nanofiber layer 104. The thickness of second nanofiber layer 104 is preferably in the range of about 5 µm to about 100 µm (a thickness of above 100 um is also possible). The second binder can be any suitable materials, e.g. poly(acrylic acid) ("PAA") polymer. The second metal compound can be any suitable disinfecting (anti-biological) material, e.g. silver (Ag), which is capable of disinfecting biological contaminants. The second metal compound in an ionic form (e.g. $Ag^+$) is capable of attracting and destroying biological contaminants. The second metal compound is attached to the second binder through a strong covalent or ionic bonding, without affecting the disinfection properties of the second metal compound. This strong bonding prevents leaching of the second metal compound from second nanofiber layer 104, thereby improves the disinfection efficiency of filtration medium 100 and provides a safe environment for the users. In some embodiments, the content of the second metal compound of second nanofiber layer 104 is from about 1 wt % to about 12 wt % which is capable of achieving about 100% disinfection of biological contaminants. As shown in FIG. 1, filtration medium 100 is configured with two anti-biological nanofiber layers (102 and 104) so as to provide a double-layer protection against the same or different types of biological contaminants. In some embodiments, second nanofiber layer 104 can be identical to first nanofiber layer 102 and comprised of the same type of anti-biological material.

Figure 3:
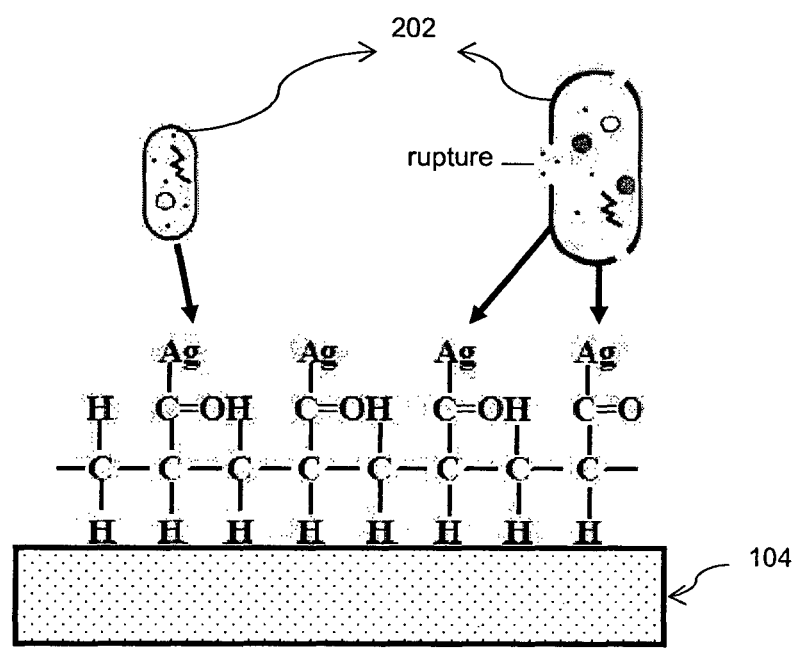
FIG. 3 is a schematic diagram illustrating disinfection (anti-biological) property of a filtration medium according to an embodiment of the present invention.

The disinfection property of second nanofiber layer 104 is illustrated in FIG. 3 with silver as the second metal compound (this illustration is applicable to first nanofiber layer 102). Silver nanoparticles are capable of disinfecting biological contaminants, e.g. bacteria, due to interaction between the positive charges of silver ions ($Ag^+$) and negatively charged bacterial surface. This interaction leads to attraction of bacteria onto ions $Ag^+$ (electrostatic attraction) and decreases in bacterial cell viability. As shown FIG. 3, ions $Ag^+$ that present on the surface of second nanofiber layer 104 interact with the membrane of bacteria 202 to rupture the membrane and empty the bacterial cell, thus destroying bacteria 202.

Figure 4:
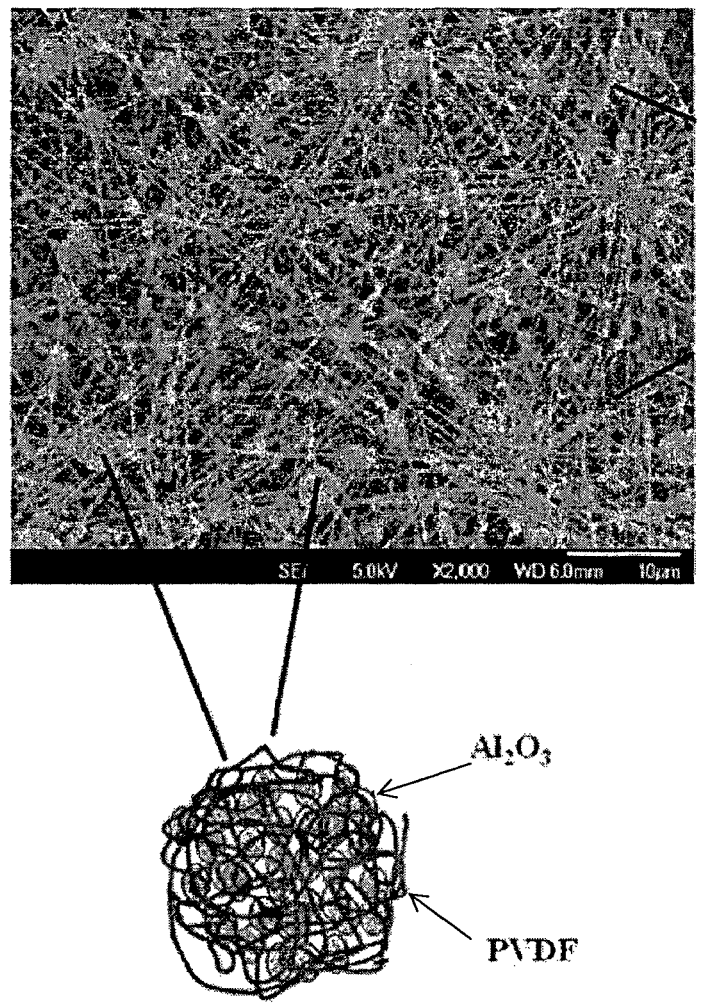
FIG. 4 is a Field Emission Scanning Electron Microscopy (FESEM) image of the middle nanofiber layer at 2000× magnification with an enlarged view of $Al_2O_3$ nanoparticles attached to PVDF polymer of a filtration medium according to an embodiment of the present invention.
Figure 5:
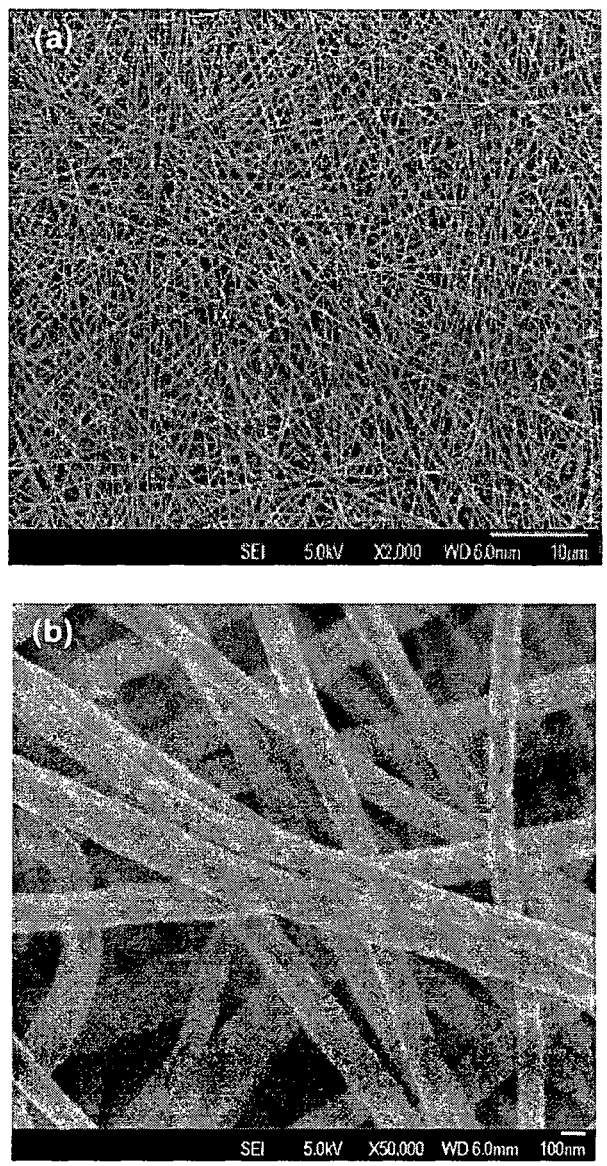
FIG. 5 is a FESEM image of the first nanofiber layer of a filtration medium at (a) low magnification (2,000×) and (b) high magnification (50,000×), according to an embodiment of the present invention.
Figure 6:
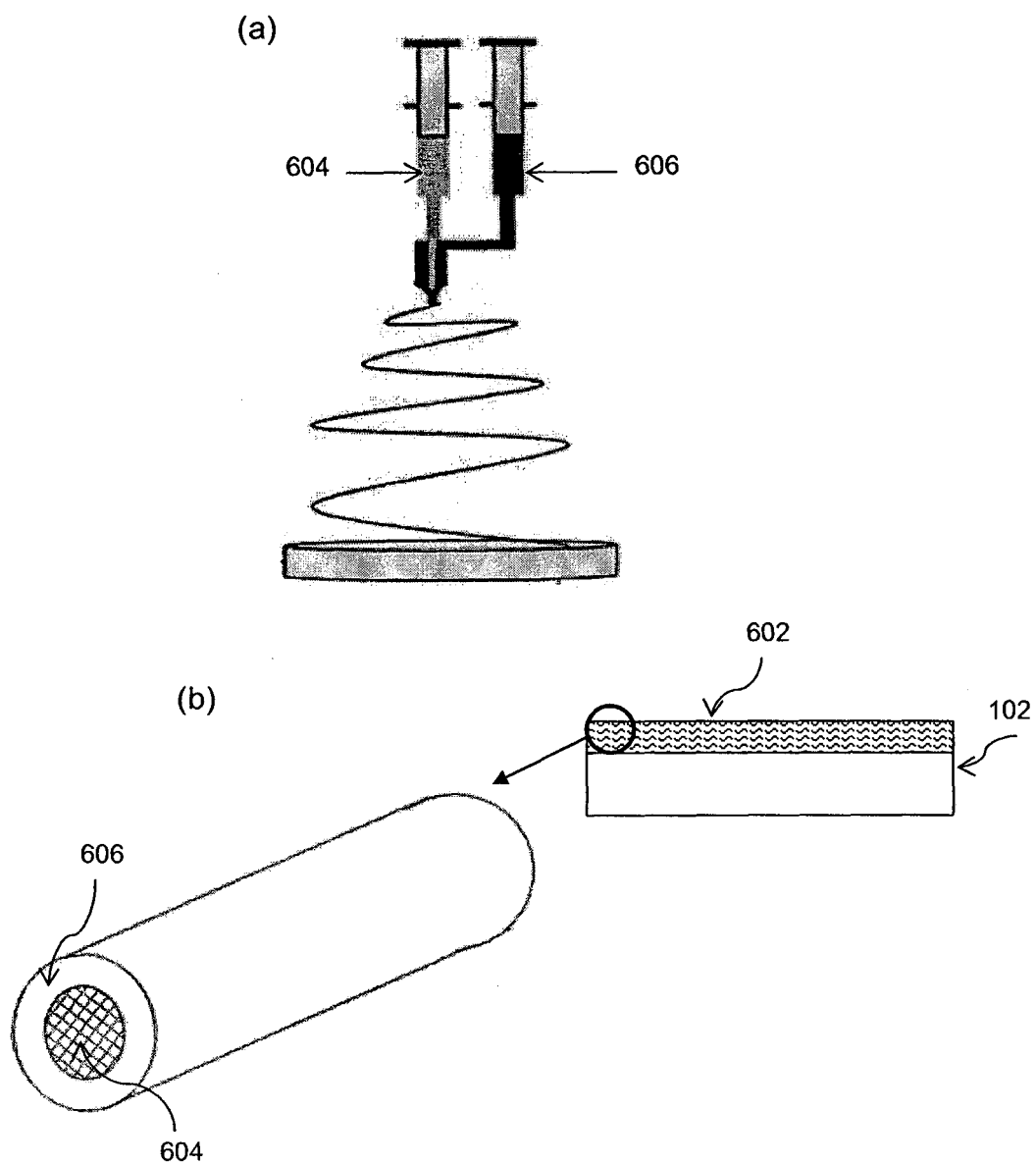
FIG. 6 (a) is a schematic diagram illustrating a core-shell electrospinning apparatus used to produce a nanofiber layer and (b) is an enlarged view of a medicinal substance in a filtration medium, according to an embodiment of the present invention.

First nanofiber layer 102 comprises a plurality of first nanofibers with each first nanofiber having a plurality of first metal nanoparticles made of the first metal compound. Similarly, second nanofiber layer 104 comprises a plurality of second nanofibers with each second nanofiber having a plurality of second metal nanoparticles made of the second metal compound. Middle nanofiber layer 106 comprises a plurality of middle nanofibers with each middle nanofiber having a plurality of metal oxide nanoparticles made of the metal oxide compound. In general, the number of nanoparticles and the size of the nanoparticle determine decontamination efficiency, in which the efficiency increases with more nanoparticles and smaller size of the nanoparticle. In some embodiments, the size of the nanoparticle is preferably in the range of about 5 nm to about 150 nm, although larger sizes are also possible. Due to small size, nanoparticles provide a large surface area-to-volume ratio for decontamination reactivity with chemical and biological contaminants. For detoxification reactivity, the number of metal oxide nanoparticles and the size of the metal oxide nanoparticle determine the rate of the catalysis mechanism. FIG. 4 shows a FESEM image of middle nanofiber layer 106 and an enlarged view of $Al_2O_3$ nanoparticles attached to PVDF polymer. FIG. 5 shows two FESEM images of first nanofiber layer 102 (applicable to second nanofiber layer 104 if same material is used) at magnifications of 2,000× and 50,000×, respectively A medicinal substance for medical applications may be incorporated in first nanofiber layer 102 and second nanofiber layer 104 (or other parts of filtration medium 100). The outer surface of the medicinal substance is coated by at least one polymer so as to protect the medicinal substance. In some embodiments, a medicinal layer comprises a plurality of medicated nanofibers may be formed in first nanofiber layer 102 or second nanofiber layer 104 with a core-shell electrospinning method, in which a medicinal substance forms the core of the medicated nanofiber and a polymer forms the shell of the medicated nanofiber. In some other embodiments, this medicinal layer may be formed as a whole first nanofiber layer 102 or second nanofiber layer 104, i.e. first nanofiber layer 102 or second nanofiber layer 104 incorporated with a medicinal substance is formed directly. Filtration medium 100 with an added medicinal substance is useful for medical applications, such as any therapeutic materials or medicines for treating respiratory diseases, asthma, chronic obstructive pulmonary disease, allergic, and etc. One skilled in the art will recognise that same or different types of medicinal substances may be used in first nanofiber layer 102 and second nanofiber layer 104. It is also envisioned that any additive may be added to the medicinal layer to provide additional desired properties, including "desorption substances" (e.g. fragrance particles) that may diffuse from the surface of the medicinal layer. FIG. 6 (b) shows medicinal layer 602 is formed in first nanofiber layer 102 by a core-shell electrospinning method as shown in FIG. 6 (a). This method produces a plurality of medicated nanofibers with medicinal substance 604 forms the core of the medicated nanofiber and polymer 606 forms the shell of the medicated nanofiber. This core-shell structure prevents medicinal substance 604 from leaching. In some embodiments, the medicinal layer may be prepared by a method that involves blending a medicinal substance with a polymer and then electrospinning the mixture solution. In some other embodiments, the medicinal layer may be prepared by dipping an electrospun nanofiber membrane into a medicinal substance and drying the nanofiber membrane.

Figure 7:
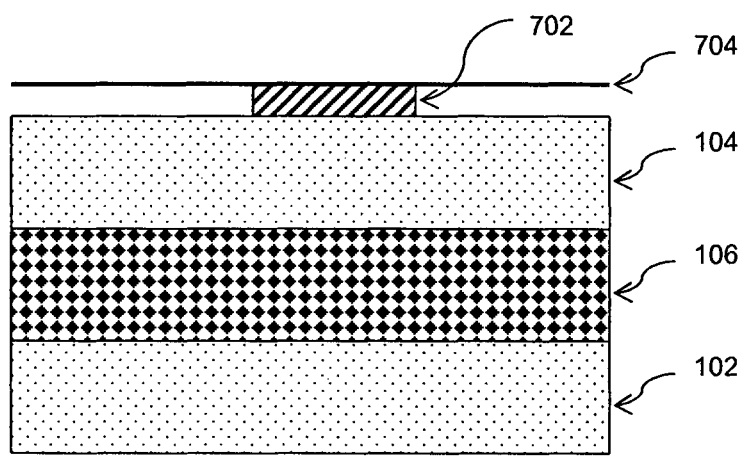
FIG. 7 is a sectional view of a filtration medium comprises a membrane sensor according to an embodiment of the present invention.

Filtration medium 100 may include a sensor for indicating the lifetime of filtration medium 100. FIG. 7 shows that sensor 702 is disposed adjacent to second nanofiber layer 104 and is covered by a protective layer 704 to prevent sensor 702 from exposure to the surroundings. Preferably, sensor 702 is a membrane type of indicator that changes colour in response to exposure to carbon dioxide. One skilled in the art will recognise that sensor 702 may be positioned at any parts of filtration medium 100, and is attachable to filtration medium 100 by any suitable methods, e.g. adhesion. Sensor 702 is made of a combination of dyes with each dye is in a different colour, e.g. bromocresol green 0.1% and methyl red 0.1%. The colour of the dye changes in response to exposure to carbon dioxide. For example in face mask application, sensor 702 will change its colour slowly as exposed to the exhaled air of the face mask wearer that contains carbon dioxide. The change of colour of sensor 702 provides an indication of the lifetime of filtration medium 100.

Membrane sensor 702 may be synthesized from nylon in the following manner. About 10 mL of 5% to 11% nylon in formic acid is electrospun at the rate of 0.5 mL/hour under the following conditions: applied voltage is from 15 kV to 30 kV; distance of the collector from the needle tip is from 100 mm to 150 mm; needle gauge is 27.5; rotation speed of the collector drum is from 100 rpm to 150 rpm; spinneret width is 50 cm; and humidity is from 60% to 65%. A membrane is formed by electrospinning and a colour solution is then coated on the membrane by a method that involves casting or dipping and drying. A combination of dyes solution of bromocresol green and methyl red in a ratio of 2:3 is used to coat the membrane to form a membrane in green colour. When the membrane is exposed to a certain amount of carbon dioxide, the membrane turns into a bright red colour and thus indicating the lifespan of the membrane. This is because carbon dioxide forms carbonic acid with the moisture and dissociates into hydrogen and bicarbonate ions. The hydrogen ion combines with water molecule to form a hydronium ion that reacts with the combination of dyes to cause the colour change.

Figure 8:
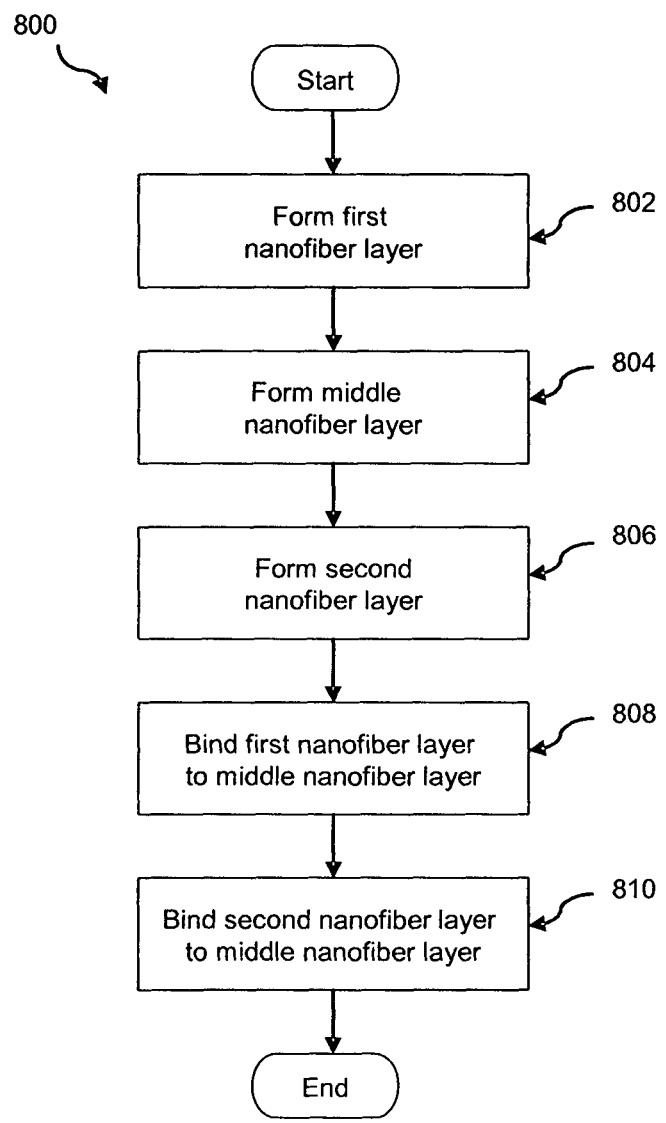
FIG. 8 is a flow diagram illustrating a method of making a filtration medium according to an embodiment of the present invention.

FIG. 8 shows a process 800 for producing a filtration medium in accordance with an embodiment of the present invention. Process 800 begins in step 802 by forming first nanofiber layer 102 which comprises a first metal compound and a first binder for covalently bonding with the first metal compound. In step 804, middle nanofiber layer 106 is formed which comprises a metal oxide compound and a polymer which acts as a binder for bonding with the metal oxide compound. Process 800 then forms second nanofiber layer 104 in step 806 which comprises a second metal compound and a second binder for covalently bonding with the second metal compound. First nanofiber layer 102 is bound to a first side of middle nanofiber layer 106 in step 808 by a suitable binding process, for example heat pressing at a temperature between 100° C. and 170° C. Second nanofiber layer 104 is bound to a second side of middle nanofiber layer 106 in step 810 by a suitable binding process, for example heat pressing at a temperature between 100° C. and 170° C. In some embodiments, layer 106 may be formed directly on layer 102 followed by forming layer 104 directly on layer 106, and then three layers 102, 106 and 104 are bound together by heat pressing in a single step.

Electrospinning is a method of using electrostatic forces to stretch a solution as it solidifies to form nanofibers. In step 802, first nanofiber layer 102 can be formed by electrospinning a mixture comprises the first metal compound, the first binder and a polymer to form a plurality of first nanofibers having a plurality of first metal nanoparticles made of the first metal compound. In step 804, middle nanofiber layer 106 can be formed by electrospinning a mixture comprises the metal oxide compound and the polymer to form a plurality of middle nanofibers having a plurality of metal oxide nanoparticles made of the metal oxide compound. In step 806, second nanofiber layer 104 can be formed by electrospinning a mixture that comprises the second metal compound, the second binder and a polymer to form a plurality of second nanofibers having a plurality of second metal nanoparticles made of the second metal compound.

Process 800 further comprises a step of adding a medicinal substance to first nanofiber layer 102 or second nanofiber layer 104 by performing a core-shell electrospinning of the medicinal substance and at least one polymer. This core-shell electrospinning method produces a plurality of medicated nanofibers with the medicinal substance forms the core of the medicated nanofiber and the polymer forms the shell of the medicated nanofiber. In some embodiments, the step of adding a medicinal substance to first nanofiber layer 102 or second nanofiber layer 104 may be performed by a core-shell electrospinning the medicinal substance and a mixture comprises a metal compound, a binder and a polymer to form a plurality of medicated nanofibers with the medicinal substance forms the core of the medicated nanofiber and the mixture forms the shell of the medicated nanofiber.

Middle nanofiber layer 106 may be formed from a solution ("Solution 2") which can be prepared in the following manner. Solution 2 is prepared by dissolving 2 wt % to 7 wt % of PVDF polymer in solvents dimethylacetamide (DMAC) and acetone (ACE) in the ratio of 2:3 and stirred for about 10 to 20 hours at about 60 degrees Celsius. When PVDF is completely dissolved in DMAC, the required amount of metal oxide compound (e.g. about 1 wt % to about 10 wt %) is added to the solution and stirred for about 24 to 48 hours at about 50 to 60 degrees Celsius until a homogenous resultant solution (Solution 2) is obtained, which is also known as "detoxification solution". Middle nanofiber layer 106 may be formed by electrospinning 1 to 10 mL Solution 2 at the rate of 0.5 to 3 mL/hour under the following conditions: applied voltage is from 15 kV to 30 kV; distance of the collector from the needle tip is from 95 mm to 150 mm; needle gauge is 27.5; rotation speed of the collector drum is from 50 rpm to 200 rpm; spinneret width is 50 cm; and humidity is from 60% to 65%. As solvents DMAC and ACE will be evaporated during electrospinning, the final weight percent of metal oxide compound presents in middle nanofiber layer 106 is up to about 67 wt % (which corresponding to about 10 wt % of metal oxide compound as initially loaded). With about 67 wt % of metal oxide compound in middle nanofiber layer 106, the filtration medium is capable of achieving about 95% detoxification of chemical contaminants. No leaching of metal oxide compound is observed. This is a remarkable result that is not easy to achieve. Simply adding more metal oxide compound in a mixture does not produce a homogenous electrospinning solution. Thus, smooth electrospun nanofibers cannot be formed and high detoxification efficiency cannot be achieved. In the present invention, in order to obtain a high loading of metal oxide compound in middle nanofiber layer 106, some additional steps have to be adopted in preparing the electrospinning solution. Specifically, when PVDF polymer is completely dissolved in DMAC, about 6 wt % to about 10 wt % of metal oxide compound is added to the solution in a small amount (e.g. 2 g) every 6 hours and stirred for about 24 to 48 hours at 60 degree Celsius. The solution as prepared is still not homogenous as some aggregates may be formed in the solution which may clog the needle tip of the electrospinning apparatus. Hence, the solution is immersed in water and is ultra-sonicated at 37 Hz for 15 to 20 minutes so as to ensure that the large and small aggregates of metal oxide compound are broken down and a homogenous solution is formed for electrospinning.

First nanofiber layer 102 and second nanofiber layer 104 may be formed from a solution ("Solution 1") which can be prepared in the following manner. Solution 1 is prepared using PVDF polymer, silver nanoparticles, and solvents dimethylformamide (DMF), DMAC and ACE. Firstly, the required amount of silver nitrate (e.g. about 1 wt % to about 12 wt %) is dissolved in DMF in the ratio of 1:19 wt % until the solution turns into blackish colour. The change of colour indicates that the silver nitrate has been reduced to silver ions. The DMF acts as an active reduction agent for silver nitrate. The silver nitrate solution is kept under UV irradiation for about 20 minutes and heated for reduction to silver ions ($Ag^+$). This reduced solution is then added to 3 wt % to 20 wt % of PVDF solution along with equal molar amounts of PAA binder (average molecular weight of 1800) with DMAC and ACE solvents of 2:3 ratio. Silver is attached to PAA through a strong covalent or ionic bonding which prevents silver from leaching. PAA also helps to reduce the unreduced silver nitrates and attach them to the nanofiber. The solution is kept at about 60 degrees Celsius for about 20 to 36 hours to ensure a homogenous solution is formed. The resultant solution (Solution 1) is also known as "disinfection solution". First nanofiber layer 102 or second nanofiber layer 104 may be formed by electrospinning 1 to 10 mL Solution 1 at the rate of 0.5 to 3 mL/hour under the following conditions: applied voltage is from 15 kV to 30 kV; distance of the collector from the needle tip is from 95 mm to 150 mm; needle gauge is 27.5; rotation speed of the collector drum is from 50 rpm to 200 rpm; spinneret width is 50 cm; and humidity is from 60% to 65%.

Disinfection Test

Example 1

The disinfection (anti-biological) property of filtration medium 100 is determined qualitatively using Zone Inhibition Test as described in the following. The biological contaminant of *Escherichia coli* (*E. coli*) bacterium is used. A nutrient agar is poured onto a sterilized petri dish and allowed it to be solidified. 100 μL of 5×105 CFU/mL *E. coli* is streaked over the culture plate and spread uniformly. Samples for the test are cut according to the size of the Kirby-Bauer disk (6 mm in diameter). A membrane of filtration medium 100 (with Ag in first and second nanofiber layers) and a control membrane (made of PVDF polymer without any anti-biological material) are placed over the solidified agar plate and are spaced out in the petri dish. The plate is incubated at 37 degree Celsius for overnight. The anti-bacterial activity is identified and estimated by a clear zone of inhibition.

Figure 9:
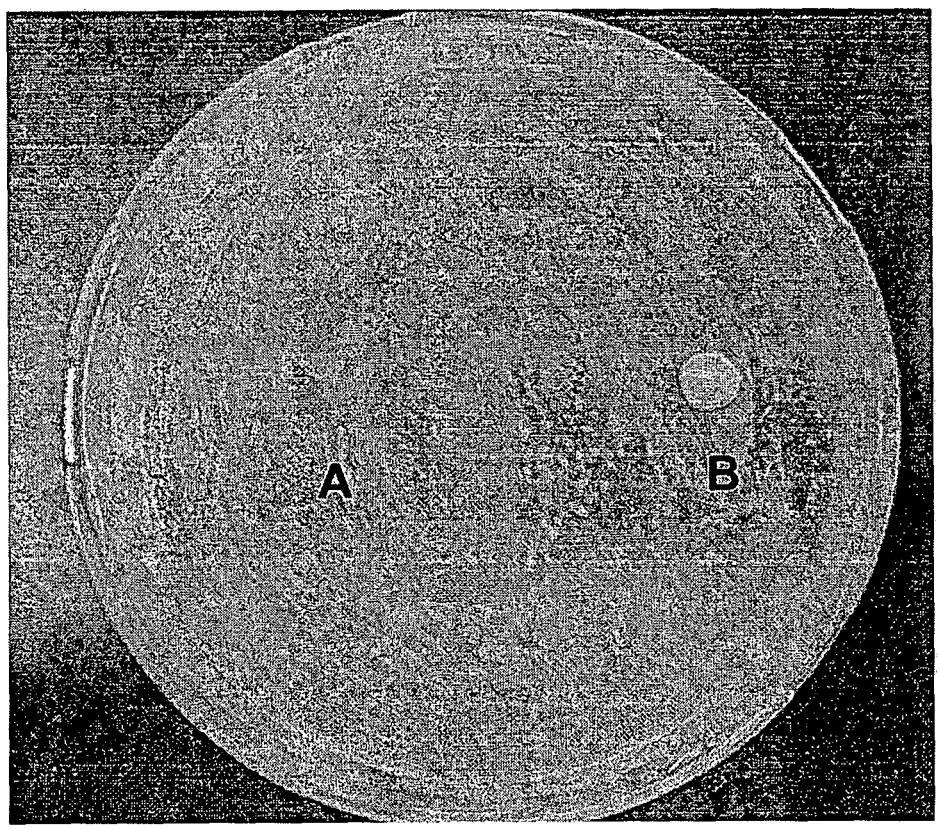
FIG. 9 is an image illustrating a qualitative test (i.e. zone inhabitation test) for disinfection property of a filtration medium according to an embodiment of the present invention.

Filtration medium 100 exhibited positive results as compared to the control membrane. Filtration medium 100 kills *E. coli* bacteria and a distinct zone of inhibition is observed (clear area with no bacterial growth) around filtration medium 100, as shown in part "A" of FIG. 9. The width of the clear zone around filtration medium 100 is about 5 mm.

This is due to the disinfection property of Ag in filtration medium 100. It is also observed that the zone of inhibition is hardly changed even if filtration medium 100 is kept for 10 days at room temperature. The results show that the disinfection property of filtration medium 100 is highly effective and durable in killing micro-organisms. In contrast, the control membrane exhibited no zone of inhibition under the same conditions as filtration medium 100 and high growth of bacterial around the control membrane is observed, as shown in part "B" of FIG. 9.

Example 2

The disinfection (anti-biological) property of filtration medium 100 is determined quantitatively using a test as described in the following. The inoculums of *E. coli* are prepared by growing strains in Lysogeny Broth (LB) medium at 37 degrees Celsius until a level of approximately 5×102 CFU/mL is obtained. A membrane of filtration medium 100 (with Ag in first and second nanofiber layers) and a control membrane (made of PVDF polymer without any anti-biological material) are introduced into the LB broth solution containing 5×102 CFU/10 mL of *E. coli*. Filtration medium 100 and the control membrane are cultured at 37 degrees Celsius in a shaker incubator for overnight at 250 rpm followed by $10^{-2}$ and $10^{-3}$ serial dilution with LB broth, respectively. 100 µL of the overnight culture and each dilution is spread uniformly on the solidified agar plate individually. The plates are incubated at 37 degrees Celsius overnight. The number of bacterial colonies (measured in CFU, i.e. colony forming unit) is counted with the SC6 STUART® colony counter to determine the antibacterial effect. The percentage efficiency is calculated using the formula:

% efficiency=$(C-T)/C \times 100$ where C is CFUs for the control membrane; and T is CFUs for filtration medium 100.

Figure 10:
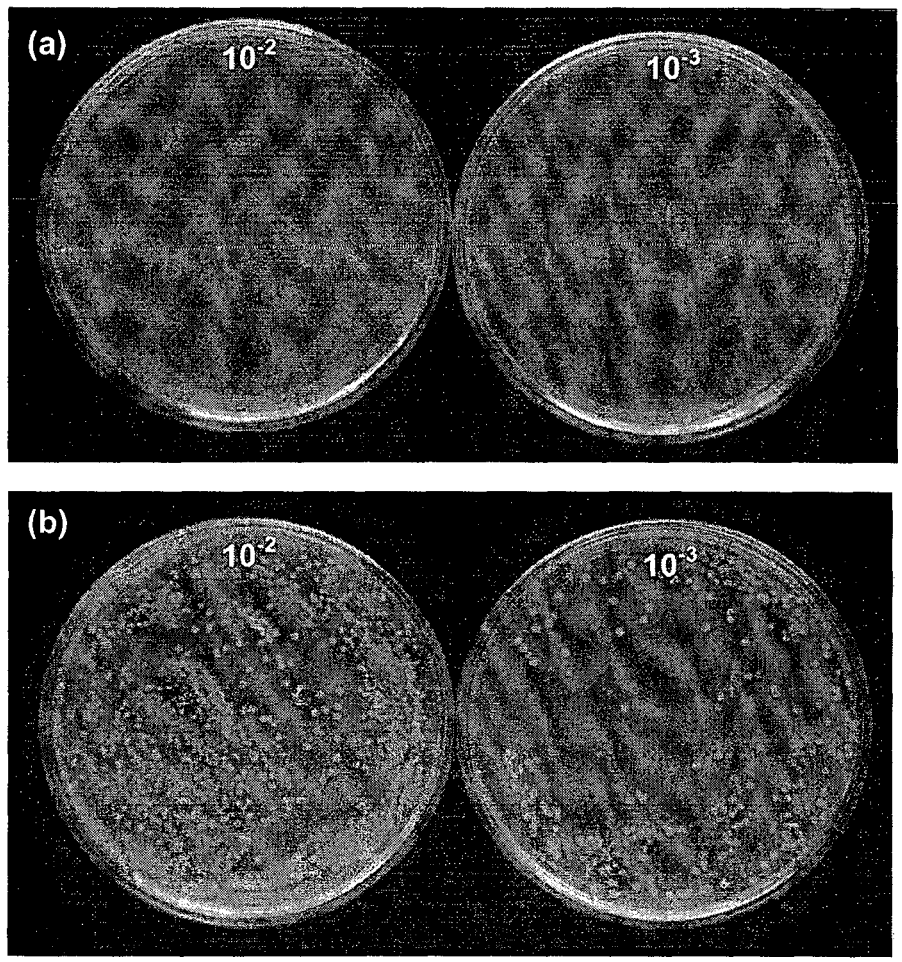
FIG. 10 is an image illustrating a quantitative test for disinfection property of a filtration medium according to an embodiment of the present invention.

The number of bacterial colonies is counted after the incubation of filtration medium 100 and control membrane in the bacterial solution. The counts are used to calculate the number of surviving bacteria. The degree of the anti-bacterial effect is the ratio of the reduction of bacterial colonies. About 100% disinfection efficiency (i.e. 0% of bacterial colonies) is found for filtration medium 100, as shown in FIG. 10 (*a*) with $10^{-2}$ dilution in the left plate and $10^{-3}$ dilution in the right plate. The results show that filtration medium 100 is active against *E. coli* bacteria. In contrast, colonies of bacteria are observed for the control membrane, as shown in FIG. 10 (*b*) with $10^{-2}$ dilution in the left plate and $10^{-3}$ dilution in the right plate.

Detoxification Test

The detoxification (anti-chemical) property of filtration medium 100 against paraoxon (a nerve agent simulant) is described in the following examples:

Example 3

Figure 11:
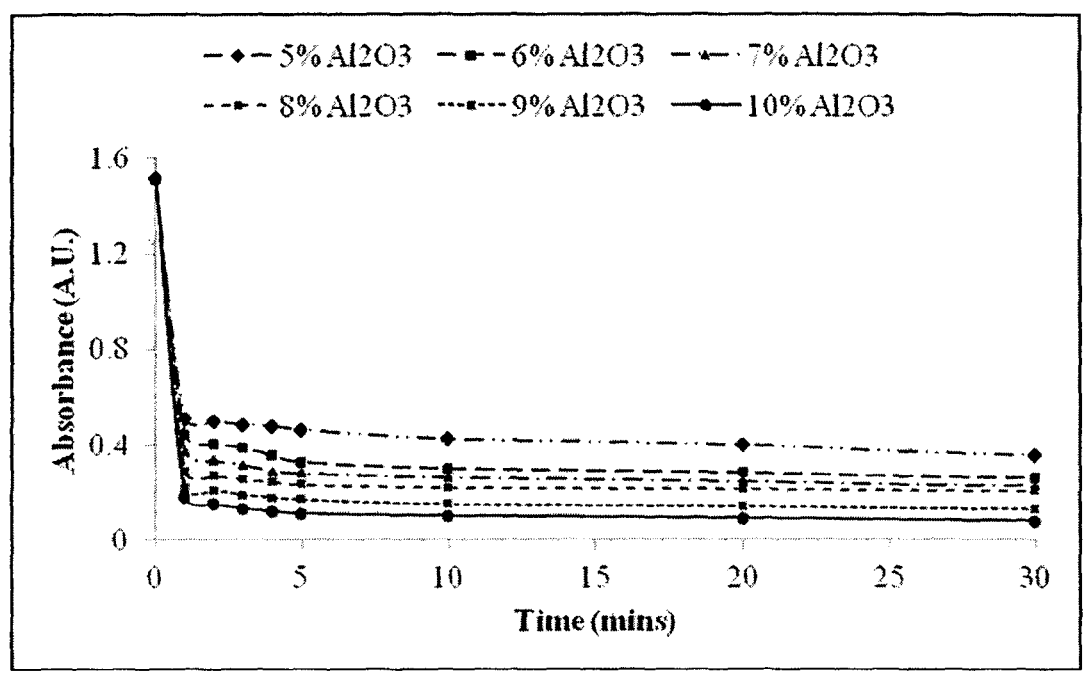
FIG. 11 is a graph illustrating UV absorbance measurements of paraoxon solution on a filtration medium with $Al_2O_3$ in various wt % according to an embodiment of the present invention.

Several membranes of filtration medium 100 comprises 5 wt %, 6 wt %, 7 wt %, 8 wt %, 9 wt % and 10 wt % of $Al_2O_3$ (and 5 wt % PVDF polymer) are prepared individually. The detoxification efficiency of these membranes against paraoxon is studied using a UV spectrophotometer. 7.5 µL of paraoxon is diluted using heptanes to make a stock solution of 30 ppm. The intensity of stock solution at maximum wavelength ($\lambda_{max}$) of 268 nm is observed by the UV spectrophotometer. 25 mL of the paraoxon solution is added to 216 cm² area of each of the membranes. UV absorbance measurements for each paraoxon solution is then carried out at 1 minute interval for a period of 5 minutes and then at 10, 20 and 30 minutes. In this study, a very low value of UV absorbance means that the paraoxon is almost fully detoxified by $Al_2O_3$ and vice verse. The graph of FIG. 11 shows that the paraoxon solution for the membrane with 10 wt % of $Al_2O_3$ has the lowest UV absorbance value since the paraoxon is almost fully detoxified by the membrane. In contrast, as expected the membrane with 5 wt % of $Al_2O_3$ shows the highest UV absorbance value as this membrane detoxifies least paraoxon. These results show that high loading of metal oxide compound is necessary in order to achieve high detoxification efficiency.

Figure 12:
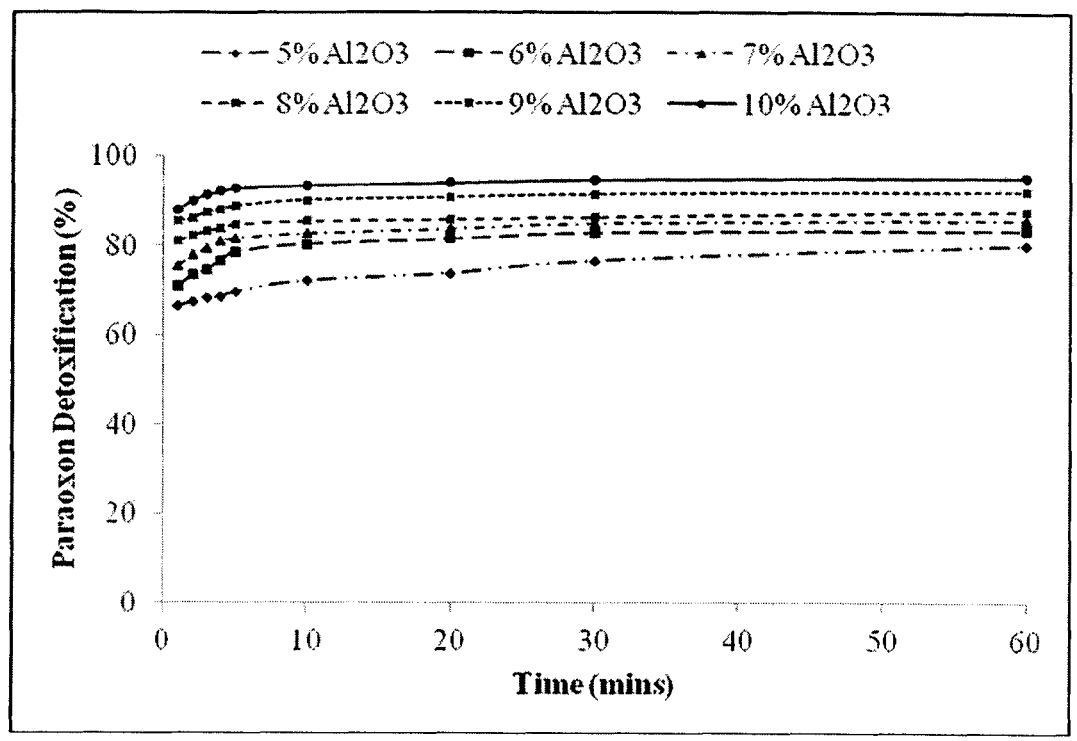
FIG. 12 is a graph illustrating paraoxon detoxification efficiency for a filtration medium with $Al_2O_3$ in various wt % according to an embodiment of the present invention.

FIG. 12 shows the efficiency in detoxifying paraoxon for filtration medium 100 in various concentrations of $Al_2O_3$. At 1 minute, the membrane of filtration medium 100 with 10 wt % of $Al_2O_3$ has detoxified about 88% of paraoxon. Detoxification percentages for other membranes with 5 wt %, 6 wt %, 7 wt %, 8 wt % and 9 wt % of $Al_2O_3$ are about 66%, 70%, 75%, 80% and 85%, respectively. These results show that detoxification activity of $Al_2O_3$ can be improved with higher loading of $Al_2O_3$. At 60 minutes, detoxification percentage for the membrane with 10 wt % of $Al_2O_3$ is about 95% which is the highest detoxification efficiency.

Example 4

Figure 13:
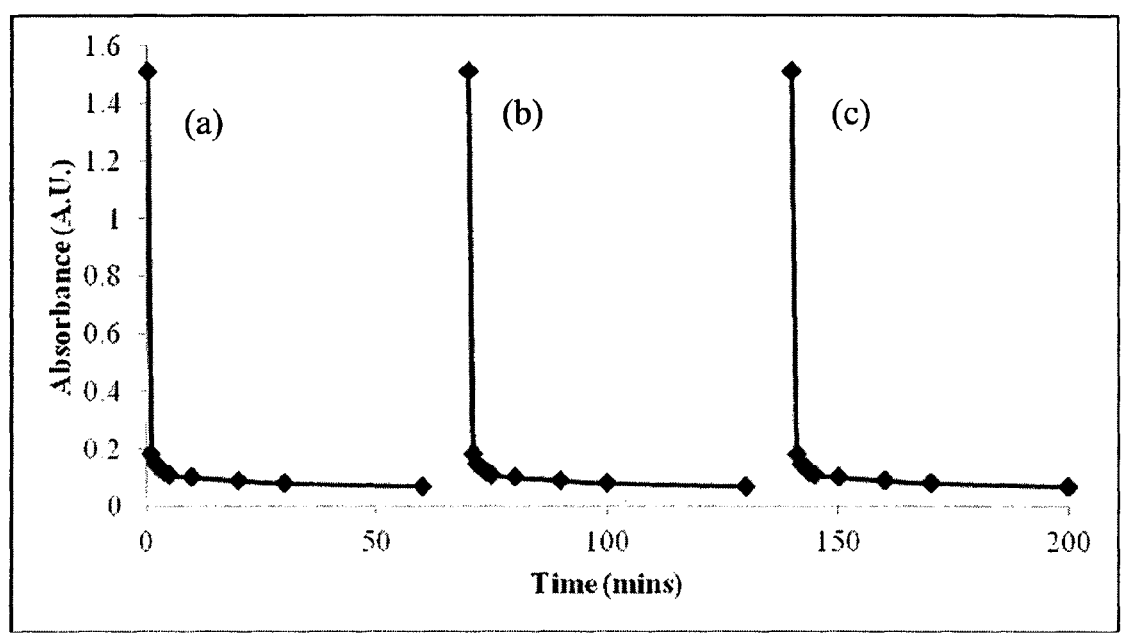
FIG. 13 is a graph illustrating UV absorbance measurements of three consecutively sets of paraoxon solution on a filtration medium according to an embodiment of the present invention.

A study of multiple detoxification activities of filtration medium 100 with 10 wt % $Al_2O_3$ is discussed. UV absorbance measurements of three consecutive sets of paraoxon solution of same concentration (i.e. 30 ppm) over a same period of time on a same membrane of filtration medium 100 are carried. Firstly, the UV absorbance for the first set of paraoxon solution is measured similar to Example 3 over a period of 60 minutes. The same membrane is then transferred to the second set of paraoxon solution and the UV absorbance is measured. Finally, the same membrane is transferred from the second set of paraoxon solution to the third set of paraoxon solution and the UV absorbance is measured. The results are shown in FIG. 13 for (a) the first set of paraoxon solution; (b) the second set of paraoxon solution; and (c) the third set of paraoxon solution, consecutively. The graphs (a), (b) and (c) are very similar to each others without showing significant changes in absorbance values. The results show that filtration medium 100 is durable and capable of detoxifying chemical contaminants for many number of times without much loss of detoxification activity as $Al_2O_3$ is regenerated during detoxification process.

Leaching Test

The leaching test of Ag and $Al_2O_3$ for filtration medium 100 is carried out using the ICP-OES (Inductively Coupled Plasma Optical Emission Spectrometry) instrument. The membrane of filtration medium 100 is immersed in water and sonicated at 37 Hz for 15 minutes, 30 minutes and 60 minutes. After sonication, the solution is filtered and the membrane of filtration medium 100 is analyzed using ICP-OES. No leaching of Ag into the solution is observed for all time intervals (due to strong covalent bonding of Ag with PAA polymer in first and second nanofiber layers). Also, no leaching of $Al_2O_3$ is observed for all time intervals (as $Al_2O_3$ forms composites with PVDF polymer and first and second nanofiber layers help to prevent $Al_2O_3$ from leaching). The results are tabulated in Table 1. For a membrane having Ag but without PAA binder (i.e. PVDF-Ag membrane), leaching of Ag is observed. For a single-layer membrane having PVDF and $Al_2O_3$ (i.e. PVDF-$Al_2O_3$ membrane) with 7 wt %, 8 wt % or 9 wt % of $Al_2O_3$, no leaching of $Al_2O_3$ is observed. However, a slight leaching of $Al_2O_3$ is observed for the PVDF-$Al_2O_3$ membrane with 10 wt % of $Al_2O_3$. In comparison, no leaching of $Al_2O_3$ is observed for filtration medium 100 even with 10 wt % of $Al_2O_3$. Thus, filtration medium 100 has a desirable zero leaching property,

TABLE 1

Leaching of Ag and $Al_2O_3$ (%)

| Time (sec) | PVDF-Ag membrane Ag | PVDF-$Al_2O_3$ membrane 7 wt % $Al_2O_3$ | 8 wt % $Al_2O_3$ | 9 wt % $Al_2O_3$ | 10 wt % $Al_2O_3$ | Filtration Medium 100 $Al_2O_3$ | Ag |
|---|---|---|---|---|---|---|---|
| 15 | 0.4 | 0 | 0 | 0 | 0.03 | 0 | 0 |
| 30 | 0.6 | 0 | 0 | 0 | 0.04 | 0 | 0 |
| 60 | 1.2 | 0 | 0 | 0 | 0.04 | 0 | 0 |

Performance Comparison with Prior Art:

Table 2 shows the performance comparison between filtration medium 100 and various commercial filters, namely N95 mask, surgical mask, 3 m air filter, AmWash filter, car filter, triboelectric media, and P3 inhaler. The properties being compared includes pressure drop (Pa), aerosol filtration efficiency (%), bacterial filtration efficiency (%), disinfection efficiency (%), detoxification efficiency (%) and metal oxide leaching. All the stated commercial filters do not have the disinfection (anti-biological) and detoxification (anti-chemical) properties. Table 2 shows that the aerosol filtration and bacterial filtration properties of filtration medium 100 are far superior than these commercial filters, and provides good permeability to airflow with desirable breathability (i.e. low pressure drop). Filtration medium 100 has a relatively good breathability, i.e. pressure drop of approximately 250 Pa even though there are three layers of nanofibers in filtration medium 100. Table 2 also shows the performance of the above stated commercial filters attached with filtration medium 100 and a single layer of detoxification nanofibers ("L1") produced by the method disclosed in US 2010/0113857 A1, respectively. The results in Table 0.2 show that the disinfection efficiency and detoxification efficiency for all the commercial filters attached with filtration medium 100 are in general, better than the commercial filters attached with L1. Further, no leaching of detoxification material is observed for the commercial filters attached with filtration medium 100. In contrast, leaching is observed for the commercial filters attached with L1. The results in Table 2 show that filtration medium 100 may be applied to any commercial filters so as to improve filtration efficiency (aerosol filtration and bacterial filtration) of the filters with additional detoxification and disinfection properties.

TABLE 2

| Filters | Pressure drop (Pa) | Aerosol filtration efficiency (%) | Bacterial filtration efficiency (%) | Disinfection efficiency (%) | Detoxification efficiency (%) | Metal oxide Leaching |
|---|---|---|---|---|---|---|
| Filtration medium 100 | 250.4 ± 20.4 | 99.0 ± 1.0 | 99.0 ± 1.0 | 99.0 ± 1 | 95.0 ± 1 | No |
| N95 mask | 231.9 ± 14.2 | 95.0 ± 1.2 | 93.0 ± 2.0 | No activity | No activity | Not tested |
| Surgical mask | 159.5 ± 13.8 | 45.5 ± 6.4 | 42.0 ± 9.5 | No activity | No activity | Not tested |
| 3M filter | 5.6 ± 5.1 | 30.0 ± 5.2 | 31.1 ± 4.2 | No activity | No activity | Not tested |
| AmWASH filter | Not tested | 14.9 ± 3.5 | 8.5 ± 5.7 | No activity | No activity | Not tested |
| Car filter | 158.4 ± 9.5 | 44.6 ± 2.8 | Not tested | No activity | No activity | Not tested |
| Triboelectric media | 4.9 ± 1.7 | 9.1 ± 1.3 | 10.5 ± 5.4 | No activity | No active ity | Not tested |
| P3 inhaler | 132.6 ± 10.7 | 69.1 ± 2.4 | 73.7 ± 3.4 | No activity | No activity | Not tested |
| N95 mask + filtration medium 100 | 325.2 ± 10.5 | 99.99 ± 0.01 | 99.0 ± 1.0 | 79.2 ± 3.8 | 70.3 ± 2.1 | No |
| N95 mask + L1 | 290.5 ± 26.7 | 99.99 ± 0.01 | 99.0 ± 1.0 | 60.5 ± 7.0 | 60.0 ± 4.3 | Yes |
| Surgical mask + filtration medium 100 | 330.5 ± 10.6 | 86.6 ± 4.6 | 80.2 ± 14.6 | 66.2 ± 3.2 | 70.0 ± 0.5 | No |
| Surgical mask + L1 | 291.6 ± 14.2 | 75.1 ± 5.7 | 70.8 ± 10.5 | 68.9 ± 1.0 | 61.1 ± 1.2 | Yes |
| 3M filter + filtration medium 100 | 172.3 ± 5.0 | 96.7 ± 2.7 | 91.5 ± 5.9 | 70.2 ± 5.5 | 72.0 ± 1.0 | No |
| 3M filter + L1 | 81.9 ± 8.4 | 67.2 ± 9.6 | 60.5 ± 10.0 | 62.5 ± 6.3 | 60.7 ± 4.0 | Yes |
| AmWASH filter + filtration medium 100 | Not tested | 78.9 ± 9.2 | 77.2 ± 7.5 | 68.8 ± 5.1 | 70.0 ± 1.0 | No |
| AmWASH filter + L1 | Not tested | 46.2 ± 7.4 | 38.5 ± 6.9 | 53.7 ± 2.5 | 60.9 ± 1.9 | Yes |
| Car filter + filtration medium 100 | 311.1 ± 15.9 | 85.8 ± 3.2 | Not tested | 72.7 ± 4.5 | 70.0 ± 0.5 | No |
| Car filter + L1 | 291.6 ± 14.2 | 75.1 ± 5.7 | Not tested | 60.9 ± 1.0 | 58.2 ± 4.2 | Yes |
| Triboelectric media + filtration medium 100 | 277.4 ± 4.2 | 90.8 ± 2.7 | 86.7 ± 9.5 | 75.5 ± 5.2 | 69.5 ± 3.1 | No |
| Triboelectric media + L1 | 180.0 ± 10.8 | 75.9 ± 5.1 | 72.7 ± 8.6 | 67.0 ± 1.2 | 59.8 ± 3.7 | Yes |
| P3 inhaler + filtration medium 100 | 212.0 ± 6.5 | 98.9 ± 1.0 | 94.2 ± 7.8 | 68.8 ± 2.8 | 71.5 ± 1.2 | No |
| P3 inhaler + L1 | 200.5 ± 10.1 | 90.1 ± 3.3 | 92.1 ± 6.4 | 62.1 ± 4.2 | 60.9 ± 4.3 | Yes |

What is claimed is:

1. A filtration medium with protective function against chemical and biological contaminants, the filtration medium comprising:
 a middle nanofiber layer having a first surface and a second surface, the middle nanofiber layer comprising roughly spun polymer nanofibers bonded to nanoparticles of a metal oxide compound, wherein the metal oxide compound is capable of reacting with the chemical contaminants through a catalysis mechanism to form at least one chemical by-product and regenerate the metal oxide compound;
 a first nanofiber layer disposed on the first surface of the middle nanofiber layer, the first nanofiber layer comprising a first metal compound and a first binder covalently bonded with the first metal compound, wherein the first metal compound is in an ionic form and is capable of attracting and destroying the biological contaminants; and
 a second nanofiber layer disposed on the second surface of the middle nanofiber layer, the second nanofiber layer comprising a second metal compound and a second binder covalently bonded with the second metal compound, wherein the second metal compound is in an ionic form is capable of attracting and destroying the biological contaminants.

2. The filtration medium of claim 1, the content of the metal oxide compound of the middle nanofiber layer is between the range of about 1 wt % to about 67 wt %, wherein the filtration medium with about 67 wt % of metal oxide compound is capable of achieving about 95% detoxification of the chemical contaminants.

3. The filtration medium of claim 1, the ratio of the metal oxide compound to the polymer of the middle nanofiber layer is about 67:33 wt %.

4. The filtration medium of claim 1, the content of the first metal compound of the first nanofiber layer is between the range of about 1 wt % to about 12 wt % which is capable of achieving about 100% disinfection of the biological contaminants.

5. The filtration medium of claim 1, the content of the second metal compound in the second nanofiber layer is between the range of about 1 wt % to about 12 wt % which is capable of achieving about 100% disinfection of the biological contaminants.

6. The filtration medium of claim 1, wherein the first nanofiber layer comprises a plurality of first nanofibers with each first nanofiber having a plurality of first metal nanoparticles made of the first metal compound.

7. The filtration medium of claim 1, wherein the second nanofiber layer comprises a plurality of second nanofibers with each second nanofiber having a plurality of second metal nanoparticles made of the second metal compound.

8. The filtration medium of claim 1, wherein the middle nanofiber layer comprises a plurality of middle nanofibers with each middle nanofiber having a plurality of metal oxide nanoparticles made of the metal oxide compound.

9. The filtration medium of claim 8, the size of each of the plurality of metal oxide nanoparticles determines the rate of the catalysis mechanism.

10. The filtration medium of claim 8, the number of the plurality of metal oxide nanoparticles determines the rate of the catalysis mechanism.

11. The filtration medium of claim 1, the thickness of the first nanofiber layer is between the range of 5 μm to 100 μm.

12. The filtration medium of claim 1, the thickness of the second nanofiber layer is between the range of 5 μm to 100 μm.

13. The filtration medium of claim 1, the thickness of the middle nanofiber layer is between the range of 10 μm to 100 μm.

14. The filtration medium of claim 1, wherein the first metal compound comprises silver.

15. The filtration medium of claim 1, wherein the second metal compound comprises silver.

16. The filtration medium of claim 1, wherein the metal oxide compound comprises aluminium oxide.

17. The filtration medium of claim 16, wherein the chemical contaminants are paraoxon which can be decomposed by aluminium oxide of the middle nanofiber layer to form the at least one chemical by-product that is at least one of p-nitrophenol, ethanol, and orthophosphoric acid.

18. The filtration medium of claim 1, wherein the first binder of the first nanofiber layer is a poly(acrylic acid).

19. The filtration medium of claim 1, wherein the second binder of the second nanofiber layer is a poly(acrylic acid).

20. The filtration medium of claim 1, wherein the polymer of the middle nanofiber layer is a polyvinylidene fluoride.

21. The filtration medium of claim 1, wherein the first nanofiber layer further comprising a first medicinal substance for medical treatment.

22. The filtration medium of claim 21, the outer surface of the first medicinal substance is being coated by at least one polymer.

23. The filtration medium of claim 1, wherein the second nanofiber layer further comprising a second medicinal substance for medical treatment.

24. The filtration medium of claim 23, the outer surface of the second medicinal substance is being coated by at least one polymer.

25. The filtration medium of claim 1, further comprising:
 a membrane sensor that changes color in response to exposure to carbon dioxide for indicating the lifetime of the filtration medium.

26. The filtration medium of claim 25, wherein the membrane sensor is made of a combination of a plurality of dyes.

27. The filtration medium of claim 1, wherein the first nanofiber layer, the second nanofiber layer, and the middle nanofiber layer are bound together by heat pressing at a temperature between 100° C. and 170° C.

28. The filtration medium of claim 1, wherein the filtration medium is in a form of membrane.

29. A method of producing a filtration medium with protective function against chemical and biological contaminants, the method comprising the steps of:
 forming a middle nanofiber layer with roughly spun nanofibers, the middle nanofiber layer comprising nanoparticles of a metal oxide compound and a polymer which acts as a binder for bonding with the metal oxide compound, wherein the middle nanofiber layer has a first surface and a second surface;
 forming a first nanofiber layer comprising a first metal compound and a first binder for covalently bonding with the first metal compound;
 forming a second nanofiber layer comprising a second metal compound and a second binder for covalently bonding with the second metal compound;
 binding the first nanofiber layer to the first surface of the middle nanofiber layer; and
 binding the second nanofiber layer to the second surface of the middle nanofiber layer.

30. The method of claim 29, wherein the step of forming the first nanofiber layer comprises:
  electrospinning a mixture comprising the first metal compound, the first binder and a polymer to form a plurality of first nanofibers.

31. The method of claim 29, wherein the step of forming the second nanofiber layer comprises:
  electrospinning a mixture comprising the second metal compound, the second binder and a polymer to form a plurality of second nanofibers.

32. The method of claim 29, wherein the step of forming the middle nanofiber layer comprises:
  electrospinning a mixture comprising the nanoparticles of the metal oxide compound and the polymer to form a plurality of roughly spun middle nanofibers.

33. The method of claim 29, wherein the step of binding the first nanofiber layer to the first side of the middle nanofiber layer comprises:
  heat pressing the first nanofiber layer to the middle nanofiber layer at a temperature between 100° C. and 170° C.

34. The method claim 29, wherein the step of binding the second nanofiber layer to the second side of the middle nanofiber layer comprises:
  heat pressing the second nanofiber layer to the middle nanofiber layer at a temperature between 100° C. and 170° C.

35. The method of claim 29, further comprising a step of:
  adding a first medicinal substance to the first nanofiber layer.

36. The method of claim 35, wherein the step of adding the first medicinal substance to the first nanofiber layer comprises:
  core-shell electrospinning the first medicinal substance and a polymer to form a plurality of medicated nanofibers, wherein the first medicinal substance forms the core of each of the plurality of medicated nanofibers and the polymer forms the shell of each of the plurality medicated nanofibers.

37. The method of claim 35, wherein the step of adding the first medicinal substance to the first nanofiber layer comprises:
  core-shell electrospinning the first medicinal substance and a first mixture comprising the first metal compound, the first binder and a polymer to form a plurality of medicated nanofibers, wherein the first medicinal substance forms the core of each of the plurality of medicated nanofibers and the first mixture forms the shell of each of the plurality of medicated nanofibers.

38. The method of claim 29, further comprising a step of:
  adding a second medicinal substance to the second nanofiber layer.

39. The method of claim 38, wherein the step of adding the second medicinal substance to the second nanofiber layer comprises:
  core-shell electrospinning the second medicinal substance and a polymer to form a plurality of medicated nanofibers, wherein the second medicinal substance forms the core of each of the plurality of medicated nanofibers and the polymer forms the shell of each of the plurality of medicated nanofibers.

40. The method of claim 38, wherein the step of adding the second medicinal substance to the second nanofiber layer comprises:
  core-shell electrospinning the second medicinal substance and a second mixture comprising the second metal compound, the second binder and a polymer to form a plurality of medicated nanofibers, wherein the second medicinal substance forms the core of each of the plurality of medicated nanofibers and the second mixture forms the shell of each of the plurality of medicated nanofibers.

* * * * *